(12) United States Patent
Antelman

(10) Patent No.: US 6,579,541 B2
(45) Date of Patent: Jun. 17, 2003

(54) OXIDATIVE FLUORINATOR COMPOUNDS AS ANTIMICROBIALS

(75) Inventor: Marvin S. Antelman, Rehovot (IL)

(73) Assignee: Marantech Holding, LLC, Providence, RI (US)

( * ) Notice: Subject to any disclaimer, the term of this patent is extended or adjusted under 35 U.S.C. 154(b) by 0 days.

(21) Appl. No.: 09/808,946

(22) Filed: Mar. 16, 2001

(65) Prior Publication Data

US 2003/0095932 A1 May 22, 2003

Related U.S. Application Data

(60) Provisional application No. 60/192,677, filed on Mar. 28, 2000.

(51) Int. Cl.⁷ .................. A01N 59/10; A01N 59/00; A01N 59/02; A01N 59/06; A01N 59/16; A01N 59/26; A61L 2/18

(52) U.S. Cl. .................. 424/646; 424/600; 424/601; 424/613; 424/617; 424/618; 424/619; 424/630; 424/631; 424/632; 424/633; 424/634; 424/635; 424/637; 424/638; 424/639; 424/640; 424/641; 424/642; 424/643; 424/644; 424/645; 424/647; 424/648; 424/649; 424/650; 424/651; 424/652; 424/653; 424/654; 424/655; 424/656; 424/673; 424/674; 424/675; 424/676; 424/682; 424/703; 424/704; 424/709; 424/713; 424/52; 514/944; 514/969; 422/37

(58) Field of Search .................. 424/600, 613, 424/617, 639, 646, 673, 703, 52, 618–619, 630–635, 637, 638, 640–656, 674–676, 682, 704, 709, 713, 601; 514/944, 969; 422/37

(56) References Cited

U.S. PATENT DOCUMENTS

4,414,990 A * 11/1983 Yost .................. 132/91
4,917,901 A    4/1990 Bourbon et al. .............. 424/673
5,026,561 A    6/1991 Bourbon et al. .............. 424/673
5,738,113 A    4/1998 Connelly .................. 128/898

FOREIGN PATENT DOCUMENTS

JP          10017452 A2    1/1998

OTHER PUBLICATIONS

Derwent Abstract, accession No. 1998–375573, abstracting RU 2099115 (Dec. 1997).*

Andres, C.J., et al., "Comparison of antibacterial properties of stannous fluoride and sodium fluoride mouthwashes," abstract, J. Dental Research, Mar.–Apr. 1974.

M. Stacey, et al., "Exhaustive Fluorinations of Organic Compounds With High–Valency Metallic Fluorides," *Adv. Fluorine Chem. 1*, pp. 166–199 (1960).

N. Bartlett, et al., "Xenon Difluoride as an Oxidative Fluorinator," *Chemical Communications*, pp. 1046–1047 (1968).

A. McKillop, et al, "Thallium in Organic Synthesis. 58. Regiospecific Intermolecular Oxidative Dehydrodimerization of Aromiatic Compounds to Biaryls Using Thallium (III) Trifluoroacetate," *J. Am. Chem. Soc.*, 102:6504–6512 (1980).

* cited by examiner

*Primary Examiner*—John Pak
(74) *Attorney, Agent, or Firm*—Pennie & Edmonds LLP

(57) ABSTRACT

The invention relates to a method and composition for destroying or inhibiting proliferation of microbes using oxidative fluorinator compounds. Fluoride salts that do not dissociate completely in aqueous solutions, such as tri- or tetravalent transition metal fluorides, inert gas fluorides, or tri- or tetravalent rare earth fluorides, are effective antimicrobial agents even at levels up to about 20 ppm, when used alone or in conjunction with a strong oxidizer.

17 Claims, No Drawings

OXIDATIVE FLUORINATOR COMPOUNDS AS ANTIMICROBIALS

CROSS-REFERENCE TO RELATED APPLICATION

This application claims priority to provisional application No. 60/192,677, filed Mar. 28, 2000.

FIELD OF THE INVENTION

The invention relates to antimicrobial compositions and their use to kill, reduce, inhibit, and prevent the proliferation of microbes.

BACKGROUND OF THE INVENTION

The application of metal fluorides to the teeth tends to retard the development of dental carries, and fluorides such as stannous fluoride are used as a component in toothpaste, powders, and oral rinses for this purpose. A combination of one or more fluoride salts and an antimicrobial material, such as chlorhexidine, may be applied to the teeth to counteract cariogenic bacteria, such as *Streptococcus Mutans*, as disclosed in U.S. Pat. No. 5,738,113 to Connelly.

The use of quaternary ammonium fluoride salts to kill microbes is disclosed in U.S. Pat. No. 5,026,561 to Bourbon et al. Various compositions, including mixtures of the quaternary ammonium fluoride and a fluoride salt such as lithium fluoride, are disclosed as components in various pharmaceutical anti-bacterial preparations such as lotions, ointments, soaps, and the like. U.S. Pat. No. 4,917,901 to Bourbon et al. discloses anti-microbial formulations that contain a mixture of a surfactant and a metal fluoride salt that is capable of generating fluoride anions.

All of the fluoride salts described above are materials that form fluoride anions, $F^-$, upon dissociation in aqueous solution. It is believed that the presence of these anions contributes to the effects described.

It is desired to find improved fluorinator antipathogenic compositions and methods of using the same to kill, reduce, inhibit, and prevent the proliferation of microbes.

SUMMARY OF THE INVENTION

The invention relates to a method for inhibiting or destroying microbes which includes contacting the microbes with a composition including an amount of at least one oxidative fluorinator compound including a fluoride that provides at least one fluoride group that does not dissociate into a fluoride anion when dissolved in an aqueous solution, wherein the amount is effective to destroy microbes or inhibit the proliferation thereof.

In a preferred embodiment, the composition further includes at least one oxidizing agent, preferably at least one of sodium persulfate or potassium persulfate. More preferably, the oxidizing agent includes potassium monopersulfate.

In another embodiment, the composition includes a combination of at least two fluorinator compounds. In a preferred embodiment, the composition includes about 0.1 to about 10 ppm by weight of the oxidative fluorinator compound. In yet another embodiment, the composition includes about 0.1 to about 50 ppm by weight sodium persulfate or potassium persulfate and about 0.1 to about 10 ppm by weight oxidative fluorinator compound.

In yet another embodiment, the oxidative fluorinator compound includes at least one of tri- or tetravalent transition metal fluorides, inert gas fluorides, tri- or tetravalent rare earth metal fluorides, oxyfluorides, or mixtures thereof. In still another embodiment, the oxidative fluorinator compound includes at least one of cobalt trifluoride, nickel tetrafluoride, manganese tetrafluoride, xenon difluoride, xenon tetrafluoride, xenon hexafluoride, or mixtures thereof. In an additional embodiment, the oxidative fluorinator compound includes an adduct of xenon fluoride, or a transition metal oxidative fluorinator. In still another preferred embodiment, the oxidative fluorinator compound includes an adduct of xenon fluoride and a rare earth metal oxidative fluorinator.

In an additional embodiment, the composition further includes an acidic stabilizer, preferably phosphoric acid. In another embodiment, the oxidative fluorinator compound completely prevents the proliferation of a microbe. The microbes include at least one of a bacteria, virus, or fungus.

The invention also relates to a method for inhibiting or destroying microbes which includes contacting the microbes with a composition including a mixture of about 0.1 to about 50 ppm by weight of an alkali metal persulfate and about 0.1 to about 20 ppm by weight of cobalt trifluoride.

The invention further relates to a composition for inhibiting or destroying microbes which includes an amount of at least one oxidative fluorinator compound, including a fluoride that provides at least one fluoride group that does not dissociate into a fluoride anion when dissolved in an aqueous solution, wherein the amount is effective to destroy microbes or inhibit proliferation thereof.

In an additional embodiment, the composition is formulated as a lotion, balm, aerosol spray, ointment, gel, shampoo, toothpaste, or mouth rinse. In a preferred embodiment, the composition further includes at least one oxidizing agent. In another embodiment, the composition includes about 0.1 to about 50 ppm by weight of an alkali metal persulfate and about 0.1 to about 20 ppm by weight oxidative fluorinator compound.

DETAILED DESCRIPTION OF THE INVENTION

The term "microbe" as used herein refers to bacteria, viruses, yeasts, and fungi. The term "antimicrobial" as used herein is intended to define a substance that is both bactericidal, i.e., kills or reduces the bacteria, and bacteriostatic, i.e., prevents or inhibits the proliferation of bacteria. Similar antimicrobial terms include virucidal and virustatic as well as fungicidal and fungustatic.

The invention provides a method for inhibiting the growth of or destroying microbes, including contacting the microbes with a composition including an effective amount of at least one oxidative fluorinator compound, the oxidative fluorinator compound including a fluoride that, when dissolved in aqueous solution, will provide at least one fluoride group that does not dissociate into a fluoride anion.

The invention provides a composition that inhibits or destroys microbes after contact of the microbe with the composition. Preferred formulations for the compositions of the invention include antibiotic compositions, disinfectant compositions, virucidal compositions, fungicidal compositions, bactericidal compositions, cosmetic compositions for body hygiene, and compositions for addition to swimming pools, hot tubs, or industrial cooling water to control the growth of bacteria.

The term "oxidative fluorinator" is a term recognized in the art and used by Bartlett and Skladky in *Chemical Communications* (1968), p. 1046, to describe fluorides that are capable of directly or indirectly generating species, e.g., elemental fluorine, which is the most electronegative and reactive element known. Thus, oxidative fluorinator compounds generate species that will react with other compounds by addition or displacement reactions, such as the replacement of hydrogen or other groups to form fluorinated compounds, particularly fluorinated hydrocarbons.

Many water-soluble fluoride salts in aqueous solution dissociate exclusively into cations and fluoride anions $F^-$. For example, NaF dissociates to $Na^+$ and $F^-$, $CoF_2$ dissociates into $Co^{2+}$ and $2 F^-$. These and other fluorides cannot be characterized as fluorinator compounds.

The oxidative fluorinator compounds of the invention, however, do not dissociate in that way. For example, cobalt trifluoride, unlike its divalent counterpart, will not yield three fluoride ions upon dissociation. Actually, $CoF_3$ is a source of elemental fluorine and as such, the dissociation product of $CoF_3$ provides at least one fluoride group that does not dissociate to a fluoride anion, and also provides, either directly or indirectly, elemental fluorine or a source of elemental fluorine. Cobalt trifluoride is described as a fluorinator in chemical synthesis. See, e.g., M. Stacey et al., *Adv. Fluorine Chem.* I, 166 (1960); A. Me Killop et al., *J. Am. Chem. Soc.* 102, 6504 (1980). Other fluorides described in the literature as fluorinator compounds include xenon fluorides, manganese tetrafluoride, and nickel tetrafluoride.

The present invention is based on the discovery that oxidative fluorinator compounds, such as described above, are effective antimicrobial agents, even when used at very low levels of less than about 20 ppm by weight in antimicrobial compositions, or when added to swimming pools or industrial cooling water at less than about 20 ppm by weight, to control microbes, such as bacteria.

Suitable oxidative fluorinator compounds of the invention include, but are not limited to, tri- or tetravalent transition metal fluorides, inert gas fluorides, such as xenon fluorides or krypton fluorides, tri- or tetravalent rare earth metal fluorides, oxyfluorides such as those of vanadium and hydrogen, or mixtures thereof.

Suitable tri- or tetravalent transition metal fluorides include cobalt trifluoride, nickel tetrafluoride, manganese tetrafluoride, and combinations thereof.

Preferred fluorides include higher atomic weight inert gas fluorides, such as krypton fluorides and xenon difluoride, xenon tetrafluoride, and xenon hexafluoride. Rare earth metal fluorides are also suitable, particularly those of the cerium subgroup such as praseodymium tetrafluoride.

In addition, crystalline adducts of xenon fluorides and metal oxidative fluorinator compounds are also preferred fluorinator compounds, such as the adduct of $XeF_6$ and $MnF_4$ ($4XeF_6 \cdot MnF_4$) and the adduct of $XeF_6$ and $PrF_4$ ($XeF_6 \cdot 4PrF_4$). Preferred oxidative fluorinator compounds forming such adducts are transition or rare earth metal tetrafluorides.

All of these represent fluorides that do not completely dissociate into ions in water and will provide reactive fluorination species having antimicrobial efficacy according to the invention when dissociated.

More preferred compositions, particularly those based on transition metal fluorides, also contain a strong oxidizer that functions to stabilize the oxidation states of the fluorides when dissolved in aqueous solutions. In particular, the transition metal fluorides can be used in combination with a strong oxidizer, preferably having a reduction potential EMF of greater than about 2 volts. Suitable oxidizers include potassium and sodium persulfates, more preferably potassium monopersulfate. The strong oxidizer is believed to stabilize the oxidation state of the more unstable metal fluorides in an aqueous medium.

Tests have shown that inert gas fluorides, such as xenon fluorides, are more stable than the transition metal fluorides and the strong oxidizer is optional for these materials to maintain their efficacy as antimicrobials. These materials, however, can also be effectively stabilized using an inorganic acid, such as nitric acid, or more preferably phosphoric acid.

The most preferred oxidative fluorinator compounds of this invention are xenon difluoride, with or without a strong oxidizer, and cobalt trifluoride when used in combination with a strong oxidizer.

The oxidative fluorinator compounds of the invention exhibit a surprising efficacy in killing, or inhibiting, or preventing the proliferation of, large colonies of various bacteria, viruses, fungi, and other microbes after only a short period of contact. The oxidative fluorinator compounds have been found to provide high, or even complete, kill rates for microbes when the microbes are contacted with solutions containing less than about 20 ppm by weight of the fluorinator, and even at concentrations of less than about 10 ppm, or from about 0.1 ppm to about 5 ppm. The exact mechanism is not known, but is believed to be related to redox or microbe fluorination. It should be understood that amounts greater than about 20 ppm of oxidative fluorinator are also included in the invention, for example, about 20 ppm to about 20,000 ppm, about 50 ppm to about 5,000 ppm, and about 100 ppm to about 1,000 ppm, in varying embodiments.

Where the oxidative fluorinator compositions according to the invention are applied to the skin, they may be combined with a carrier at an amount from about 5 ppm to about 500,000 ppm, more preferably from about 50 ppm to about 250,000 ppm of the oxidative fluorinator composition, based on the weight of the carrier. In various embodiments, the compositions are provided in amounts from about 400 ppm to about 100,000 ppm, from about 1,000 ppm to about 70,000 ppm, from about 10,000 ppm to about 50,000 ppm, or from about 20,000 ppm to about 40,000 ppm. In one preferred embodiment, the compositions are formulated with about 25,000 ppm to about 35,000 ppm of oxidative fluorinator compound. It will be readily understood by those of ordinary skill in the art that 1 ppm of oxidative fluorinator compound is approximately equivalent to 1 mg/L. The compositions, when applied topically, can be applied to the skin about 1 to about 3 times per day until the condition is suitably cured or satisfactorily controlled. In one embodiment, the composition may generally be topically applied at a dosage level of from about 1 mg to about 1000 mg per $cm^2$ of skin surface, preferably about 10 mg to about 500 mg per $cm^2$ of skin surface. A preferred carrier includes petroleum jelly, such as white petroleum jelly.

In practical use, oxidative fluorinator, or a derivative thereof, can be combined as the active ingredient in intimate admixture with a pharmaceutical carrier according to conventional pharmaceutical compounding techniques. The carrier may take a wide variety of forms and may include a number of components depending on the form of preparation desired for administration. The compositions of the present invention may include, but are not limited to, suspensions, solutions and elixirs; aerosols; or carriers, including, but not limited to, starches, sugars, microcrystalline cellulose, diluents, granulating agents, lubricants, binders, disintegrating agents, and the like.

The fluoriator compounds of the present invention (and the stabilizer) may be added to water to form antimicrobial solutions, such as in a swimming pool, a hot tub, or an industrial cooling water system. The fluorinator compounds may further be formulated with any suitable carrier materials, such as surfactants, or other additives, for the manufacture of antimicrobial bar soaps and hand soaps. Other carriers include excipients, such as glycols, fatty acids and acid eaters, petroleum jelly, gums, lanolin, starches, and the like, that are normally used to prepare aqueous-based lotions, balms, aerosol sprays, ointments, gels, shampoos, toothpaste, mouth rinses, and like preparations for topical application. The fluorinator compounds may also be formulated into anti-bacterial cleaning compositions (liquids or powders) or laundry detergents. The fluorinator compounds may further be formulated into compositions containing one or more additional antimicrobial agents, such as antibiotics or other germicides.

A preferred route of administration of the oxidative fluorinator compounds of the invention is topically, e.g., either directly as a powder or in non-sprayable or sprayable form. Non-sprayable forms can be semi-solid or solid forms including a carrier indigenous to topical application and preferably having a dynamic viscosity greater than that of water.

Suitable formulations include, but are not limited to, suspensions, emulsions, creams, ointments, powders, liniments, salves and the like. If desired, these may be sterilized or mixed with one or more of any available auxiliary agents, carriers, or excipients, e.g., thixotropes, stabilizers, wetting agents, and the like, and combinations thereof. One or more thixotropic agents can be included in types and amounts sufficient to increase adhesion of topically applied compositions of the invention to the skin, so as to inhibit or prevent runoff or other loss of the composition from the treatment zone on the skin. Preferred vehicles for non-sprayable topical preparations include ointment bases, e.g., polyethylene glycol-1000 (PEG-1000); conventional ophthalmic vehicles; creams; and gels, as well as petroleum jelly and the like. In one more preferred embodiment, the carrier includes a petroleum jelly. In another preferred embodiment, the carrier is formulated as a cream, gel, or lotion. In another preferred embodiment, the carrier is about 3 weight percent active ingredient, about 36 weight percent heavy mineral oil, about 47 weight percent petroleum jelly, and about 14 weight percent Tivawax P, available from Tivian Laboratories, Inc., of Providence, R.I. In yet another preferred embodiment, the carrier may be a dry powder compositions, such as with about 5 weight percent active ingredient and about 95 weight percent bismuth subgallate. These topical preparations may also contain emollients, perfumes and/or pigments to enhance their acceptability for various usages.

The pharmaceutical compositions for use in the present invention include oxidative fluorinator, or a derivative thereof, as the active ingredient, and may also contain a pharmaceutically acceptable carrier, and optionally, other therapeutic ingredients. Suitable derivatives include any available "pharmaceutically acceptable salts," which refer to a salt prepared from pharmaceutically acceptable non-toxic acids including inorganic acids, organic acids, solvates, hydrates, or clathrates thereof. Examples of such inorganic acids are nitric, sulfuric, lactic, glycolic, salicylic, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, paratoluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Particularly preferred acids are lactic, glycolic, and salicylic acids.

In addition to the common dosage forms set out above, the compounds of the present invention may also be administered by controlled release means, delivery devices, or both, as are well known to those of ordinary skill in the art, such as those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, the disclosures of which are hereby incorporated herein by express reference thereto. These pharmaceutical compositions can be used to provide slow or controlled-release of the active ingredient therein using, for example, hydropropylmethyl cellulose in varying proportions to provide the desired release profile, other polymer matrices, gels, permeable membranes, osmotic systems, multilayer coatings, microparticles, liposomes, microspheres, or the like, or a combination thereof. Suitable controlled-release formulations available to those of ordinary skill in the art, including those described herein, may be readily selected for use with the oxidative fluorinator compounds of the invention. Thus, single unit dosage forms suitable for topical administration, such as gels, lotions, cremes, and the like, that are adapted for controlled-release are encompassed by the present invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include: 1) extended activity of the drug; 2) reduced dosage frequency; and 3) increased patient compliance.

Most controlled-release formulations are designed to initially release an amount of drug that promptly produces the desired therapeutic effect, and gradual and continual release of other amounts of drug to maintain this level of therapeutic effect over an extended period of time. In order to maintain this constant level of drug in the body, the drug should be released from the dosage form at a rate that will replace the amount of drug being metabolized and excreted from the body.

The controlled-release of the active ingredient may be stimulated by various inducers, for example pH, temperature, enzymes, water, or other physiological conditions or compounds. The term "controlled-release component" in the context of the present invention is defined herein as a compound or compounds, including polymers, polymer matrices, gels, permeable membranes, liposomes, microspheres, or the like, or a combination thereof, that facilitates the controlled-release of the active ingredient (e.g., oxidative fluorinator) in the pharmaceutical composition.

EXAMPLES

These and other aspects of the present invention may be more fully understood with reference to the following examples, which are merely illustrative of the preferred embodiments of the present invention, and are not to be construed as limiting the invention, the scope of which is defined by the appended claims. Unless otherwise indicated, antimicrobial evaluations of the various fluorinator compounds tested were performed versus control samples in cultures in accordance with the protocol as set forth in AOAC (15th) 1990:965:13 at colony densities indicated in the examples.

Example 1

Contaminated water was prepared and measured to have AOAC coliform counts averaging 37.4 colony forming units per milliliter (cfu/mL). The water was treated by first adding crystal potassium monopersulfate (KPS) stabilizer, commercially available from E.I. DuPont de Nemours & Co. Corp. as OXONE®, and xenon difluoride ($XeF_2$). The concentration in solution of the KPS and $XeF_2$ was about 20 PPM and about 2 PPM respectively, and the pH of the treated solution was about 7. Culture test versus controls showed that the coliform were inhibited by about 73% after 5 minutes of exposure time and by about 77% after 10 minutes of exposure time.

Example 2

Aqueous solutions were prepared having a salmonella contamination at a cell density of about 500,000 cfu/mL. Two solutions of $XeF_2$ were prepared: one as a 1% solution in 85% phosphoric acid stabilizer, and a second solution containing no stabilizer. The materials were cultured versus controls at concentrations of about 2 ppm and about 4 ppm $XeF_2$ and at a pH of about 9. After ten minutes of exposure time, the phosphoric acidstabilized $XeF_2$ culture exhibited an inhibition of about 93.2%, while the $XeF_2$ culture had an inhibition of only about 13.2%. At about 4 ppm $XeF_2$, however, the former exhibited an inhibition of 100% and the latter about 96.4%.

Example 3

The inhibition % of $CoF_3$ stabilized with about 10 ppm KPS at a pH of about 7 was evaluated as in Example 2 against *E. Coli* at various cell densities. The results are shown in Table 1.

TABLE 1

|  | Sample 1 | Sample 2 | Sample 3 |
| --- | --- | --- | --- |
| Cell Density (cfu/mL) | 200,000 | 420,000 | 600,000 |
| $CoF_3$ (ppm) | 2 | 1 | 0.5 |
| Contact Time (min.) | 0.5 | 10 | 10 |
| Inhibition (%) | 98 | 100 | 97.5 |

Example 4

A hand soap base was prepared comprising an aqueous mixture of coconut fatty acid amide and sodium lauryl sulfate surfactants. $XeF_2$ was incorporated into the hand soap base at a level of about 5 ppm and four separate cultures containing various microbes at a level of about 320,000 cfu/mL were evaluated. Results after 30 seconds of exposure are shown in Table 2.

TABLE 2

| Microbe | *Enterococcus Faecalis* | *Staph Aureus* | *E. Coli* | *Salmonella* |
| --- | --- | --- | --- | --- |
| Strain/Resistance | Vancomycin | Methicillin | ATCC 81377 | ATC 14 |
| Inhibition (%) | 99.9 | 99.5 | 99.9 | 99.9 |

Example 5

An industrial cooling tower containing about 1,000 gallons of water tested positive for a high bacterial colony count using a standard immersion test kit. KPS and $CoF_3$ were added to the water at levels of about 10 ppm and about 1 ppm, respectively. After 24 hours, the immersion kit test was performed again on the cooling tower water and indicated complete destruction of bacterial colonies.

Thus, the data show that the oxidative fluorinator compounds of this invention are capable of killing microbes up to at least about 1,000,000 cfu/mL at concentrations of up to about 10 ppm. The data further indicate antimicrobial action against Gram Negative and Gram Positive microorganisms as well as yeast and mold.

It will be understood that the claims are intended to cover all changes and modifications of the preferred embodiments of the invention, herein chosen for the purpose of illustration, which do not constitute a departure from the spirit and scope of the invention.

What is claimed is:

1. A method for destroying or inhibiting proliferation of microbes which comprises contacting the microbes with a composition comprising (1) an amount of at least one oxidative fluorinator compound that provides at least one fluoride group that does not dissociate into a fluoride anion when dissolved in an aqueous solution, wherein the amount of the compound is effective to destroy the microbes or inhibit proliferation, and (2) at least one oxidizing agent.

2. The method of claim 1, wherein the at least one oxidizing agent comprises at least one of sodium persulfate or potassium persulfate.

3. The method of claim 2, wherein the at least one oxidizing agent comprises potassium monopersulfate.

4. The method of claim 1, wherein the composition contains a combination of at least two different fluorinator compounds.

5. The method of claim 1, wherein the composition contains about 0.1 to about 10 ppm by weight of the fluorinator compound.

6. The method of claim 2, wherein the composition comprises about 0.1 to about 50 ppm by weight sodium persulfate or potassium persulfate and about 0.1 to about 10 ppm by weight said fluorinator compound.

7. The method of claim 1, wherein the fluorinator compound comprises at least one of tri- or tetravalent transition metal fluorides, inert gas fluorides, tri- or tetravalent rare earth metal fluorides, oxyfluorides, or mixtures thereof.

8. The method of claim 1, wherein the fluorinator compound comprises at least one of cobalt trifluoride, nickel tetrafluoride, manganese tetrafluoride, xenon difluoride, xenon tetrafluoride, xenon hexafluoride, or mixtures thereof.

9. The method of claim 1, wherein the fluorinator compound comprises an adduct of xenon fluoride, or a transition metal oxidative fluorinator compound.

10. The method of claim 1, wherein the fluorinator compound comprises an adduct of xenon fluoride and a rare earth metal oxidative fluorinator compound.

11. The method of claim 1, wherein the composition further comprises an acidic stabilizer.

12. The method of claim 11, wherein the acidic stabilizer comprises phosphoric acid.

13. The method of claim 1, wherein the microbes comprise at least one of a bacteria, virus, or fungus.

14. A method for destroying or inhibiting proliferation of microbes which comprises contacting the microbes with a composition comprising a mixture of about 0.1 to about 50 ppm by weight of an alkali metal persulfate and about 0.1 to about 20 ppm by 30 weight of cobalt trifluoride.

15. A composition for destroying or inhibiting proliferation of microbes which comprises (1) at least one oxidative fluorinator compound that provides at least one fluoride group that does not dissociate into a fluoride anion when dissolved in an aqueous solution, wherein the compound is present in an amount effective to destroy microbes or inhibit proliferation, and (2) at least one oxidizing agent.

16. The composition of claim 15 formulated as a lotion, balm, aerosol spray, ointment, gel, shampoo, toothpaste, or mouth rinse.

17. The composition of claim 15, comprising about 0.1 to about 50 ppm by weight of an alkali metal persulfate and about 0.1 to about 20 ppm by weight fluorinator compound.

* * * * *